United States Patent
Irrgang et al.

(10) Patent No.: US 6,497,866 B2
(45) Date of Patent: *Dec. 24, 2002

(54) METHOD FOR PRODUCING A POMADE EFFECT BASED ON A SINGLE-PHASE, FOAM-FORMING HAIR TREATMENT COMPOSITION

(75) Inventors: Bernhard Irrgang, Anton; Thomas Karlen, Bern, both of (CH)

(73) Assignee: Wella Aktiengesellschaft, Darmstadt (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 12 days.

(21) Appl. No.: 09/802,136

(22) Filed: Mar. 8, 2001

(65) Prior Publication Data

US 2001/0019711 A1 Sep. 6, 2001

Related U.S. Application Data

(62) Division of application No. 09/338,619, filed on Jun. 23, 1999, now abandoned.

(30) Foreign Application Priority Data

Jun. 26, 1998 (DE) .......................................... 198 28 643

(51) Int. Cl.[7] .............................. A61K 7/08; A61K 7/06
(52) U.S. Cl. ................. 424/70.24; 424/70.1; 424/70.19; 424/70.22; 424/70.31
(58) Field of Search ............................. 424/70.1, 70.19, 424/70.22, 70.24, 70.31, 421

(56) References Cited

U.S. PATENT DOCUMENTS

| | | | |
|---|---|---|---|
| 3,948,943 A | * | 4/1976 | Eberhardt et al. |
| 5,364,031 A | * | 11/1994 | Taniguchi et al. |
| 5,429,815 A | * | 7/1995 | Faryniarz et al. |
| 5,635,469 A | * | 6/1997 | Fowler et al. |
| 5,826,546 A | * | 10/1998 | Epstein |
| 6,165,444 A | * | 12/2000 | Dubief et al. |
| 6,190,647 B1 | * | 2/2001 | Karlen et al. |

FOREIGN PATENT DOCUMENTS

| WO | WO-94/17783 A2 | * | 8/1994 |
|---|---|---|---|

* cited by examiner

Primary Examiner—Thurman K. Page
Assistant Examiner—Humera N. Sheikh
(74) Attorney, Agent, or Firm—Michael J. Striker

(57) ABSTRACT

The method of obtaining a pomade effect on hair includes providing a foam pump apparatus for making a foam from a single-phase composition, which contains at least one anionic, carboxylate-group containing surfactant compound, preferably a sulfosuccinate, and at least one nonionic emulsifier; then generating a foam from the single-phase composition by operating the foam pump apparatus; and working at least a portion of the foam into the hair without subsequently rinsing the hair in order to provide the pomade effect.

15 Claims, No Drawings

METHOD FOR PRODUCING A POMADE EFFECT BASED ON A SINGLE-PHASE, FOAM-FORMING HAIR TREATMENT COMPOSITION

CROSS-REFERENCE

This is a division of U.S. patent application Ser. No. 09/338,619, filed Jun. 23, 1999, Abandoned.

BACKGROUND OF THE INVENTION

1. Field of the Invention

The subject matter of the present invention is a method of treating hair with a foam made from a single-phase, foam-forming hair treatment composition to produce a pomade effect, especially a fixing effect and luster in the treated hair.

2. Prior Art

Research in the field of hair treatment compositions has included study of preparations in the form of pomades for many years. These pomades facilitate hair shaping and increase the luster and hold of a hairstyle. Pomades are usually applied as non-transparent masses in the form of creamy emulsions or gels. However the emulsions or gels are difficult to distribute evenly on the hair, so that hair styling is difficult, especially when only small sections of the hair are treated with this agent.

The products conventionally employed to produce a pomade effect, which means to simultaneously produce an intense luster and hold, have a high proportion of water-insoluble materials, such as fatty bodies. Because of these fatty bodies however the hair is strongly loaded and the product is removed only with difficulty by means of a shampoo to the extent that the hair does not have a residue. Furthermore this type of product suffers from the problem of undesirable separation of water and fat phase.

SUMMARY OF THE INVENTION

It is an object of the present invention to provide a method with which an intense pomade effect can be obtained, whereby the typically negative or poor properties of the prior art compositions, such as poor distributability on the hair, strong load of the hair, poor washability from the hair and phase separation of the product are avoided.

Pomade in the form of foam that breaks up when worked into the hair or on styling the hair offers a better possibility for application to hair.

Low or average viscosity masses with pomade properties can be applied with the help of aerosol foam. The advantage of a propellant aerosol product is that it is very easy to produce foam with it, even with small amounts of only poorly foaming contents. It is however a disadvantageously difficult problem to stabilize the propellant gas in the aqueous phase for packing the composition as a single-phase product. Phase separation can change the properties important to the composition's action as a pomade as well as its aesthetic properties. If the aerosol product should be packaged in a transparent container, only glass is considered for use as a packaging material. The packaging of an aerosol product in a glass container however results in a potential safety problem or a risk.

Foaming without propellant gas occurs in a simple way by the use of a strongly foaming surfactant compound selected from the classes of anionic surfactants, amphoteric surfactants or nonionic surfactants. The disadvantage of using these surfactants in concentrations which are required so that the pomade composition will be in the form of a foam is that when the foam composition is applied to the hair it does not break up. Furthermore an after-foaming occurs on the hair, as it does similarly with a shampoo, which is undesirable for application of a pomade. Furthermore pomade masses, which contain large proportions of these surfactants are too viscose to guarantee that good foaming action can be obtained without the help of a propellant gas. Dilution with organic solvent leads of course to a reduction in viscosity, however a drastic reduction in foamability also occurs because of the dilution. If the pomade composition is diluted with water until it reaches a viscosity at which it is easy to form foam, this leads to a reduction in the pomade effect.

According to the invention these difficulties are overcome by providing a product or article of manufacture for hair treatment consisting of A) single-phase composition containing
    a1) at least one anionic, carboxylate-group-containing surfactant compound, and
    a2) at least one nonionic emulsifier; in combination with B) an apparatus for making a foam from the single-phase composition (A).

The composition provides outstanding foam without the use of a propellant gas and can be worked into the hair satisfactorily without a disturbing after-foam formation. It imparts good shapability, a long-lasting luster and a long-lasting soft feel to the hair.

The carboxylate-group-containing surfactant compound or compounds is or are preferably present in the composition in an amount of from 0.1 to 30 percent by weight, especially preferably in an amount of from 1 to 10 percent by weight. The preferred carboxylate-group-containing surfactant compound or compounds is or are sulfosuccinate or sulfosuccinates, sulfosuccinamate or sulfosuccinamates, carboxylated fatty alcohol ethoxylate or ethoxylates, carboxylated fatty acid amide ethoxylate or ethoxylates or their mixtures.

Preferably the surfactant compound (a1) has the general formula (I):

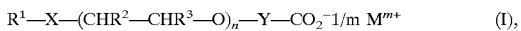

wherein —X— represents —COO—, —CONH—, —O— or —NH—; —Y— represents an alkylene group, preferably with 1 to 4 carbon atoms, especially a methylene group or —Y—CO$_2^-$ represents a sulfosuccinate group; R$^1$ represents an unsaturated or saturated, branched or non-branch hydrocarbon group, preferably with 5 to 20 carbon atoms, which can be substituted with at least one hydroxy group, or R$^1$—X— represents an alkoxylated or non-alkoxylated alkyl citrate group; R$^2$ and R$^3$, independently of each other, represent hydrogen or a methyl group; n is the degree of alkoxylation and is between 0 and 20, preferably between 0 and 10; M represents one or more counter ions which neutralize the negative charge on the anion, for example a metal ion or a quaternary ammonium cation, and m is the valence of the counter ion M. If —Y—CO$_2^-$ stands for a sulfosuccinate group, it is preferably in the form —C(O)—CHR$^4$—CHR$^5$—CO$_2^-$, wherein one of the R$^4$ and R$^5$ is hydrogen and the other is SO$_3^-$. When R$^1$—X represents an alkoxylated or non-alkoxylated alkyl citrate group, it is preferably in the form

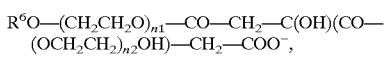

wherein $R^6$ represents a saturated or unsaturated, branched or non-branched hydrocarbon group preferably with 5 to 20 carbon atoms, which can be substituted with at least one hydroxy group, and n1 and n2 are the degrees of alkoxylation, each of which is between 0 to 10, preferably between 0 and 5.

As carboxylate-group-containing surfactant compound or compounds the following are particularly suitable for ingredient a1:

compounds of the formula (II)

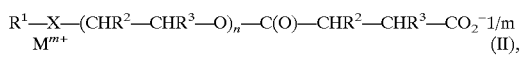

$$R^1-X-(CHR^2-CHR^3-O)_n-C(O)-CHR^2-CHR^3-CO_2^-1/m\ M^{m+} \quad (II),$$

wherein $R^2$, $R^3$, n, m and M have the same significance as above and wherein at least one of the groups $R^2$ and $R^3$ represents hydrogen; $R^1$ represents a saturated or unsaturated, branched or non-branched hydrocarbon group, preferably with 5 to 20 carbon atoms, which can be substituted with at least one hydroxy group; —X— represents —COO—, —CONH— or —NH— and the groups $R^4$ and $R^5$, independently of each other, represent hydrogen or $SO_3^-$, but at least one of the groups must be hydrogen.

Suitable sulfosuccinates are, for example, known under the following INCI names disodium ricinol amido MEA sulfosuccinate, disodium cocamido MIPA sulfosuccinate, disodium PEG-4 cocamido MIPA-sulfosuccinate, disodium PEG-5 lauryl citrate sulfosuccinate, disodium cocamido PEG-3 sulfosuccionate, disodium laneth-5 sulfosuccinate or disodium undecylene amido MEA-sulfosuccinate. A suitable sulfosuccinamate is for example disodium tallow sulfosuccinamate (INCI name).

alkyl citrates of the formula (III),

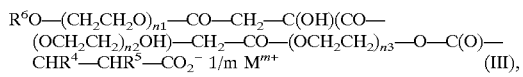

$$R^6O-(CH_2CH_2O)_{n1}-CO-CH_2-C(OH)(CO-\ (OCH_2CH_2)_{n2}OH)-CH_2-CO-(OCH_2CH_2)_{n3}-O-C(O)-\ CHR^4-CHR^5-CO_2^-\ 1/m\ M^{m+} \quad (III),$$

wherein m and M have the significance as defined above; $R^6$ represents a saturated or unsaturated, branched or non-branched hydrocarbon group preferably with 5 to 20 carbon atoms, which can be substituted with at least one hydroxy group, the groups $R^4$ and $R^5$, independently of each other, represent hydrogen or $SO_3^-$, but at least one of both groups must be hydrogen; and n1, n2 and n3 each represent the respective degree of alkoxylation and each is a respective value between 0 and 10, preferably between 0 and 5.

A suitable alkyl citrate sulfosuccinate is, for example, designated by the INCI name disodium PEG-10 lauryl citrate sulfosuccinate or disodium PEG-5 lauryl citrate sulfosuccinate (REWOPOL® SB CS 50 of Witco Surfactants GmbH, Germany).

—compounds of the general formula (IV)

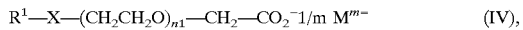

$$R^1-X-(CH_2CH_2O)_{n1}-CH_2-CO_2^-1/m\ M^{m-} \quad (IV),$$

wherein n, m and M have the same significance as above; $R^1$ represents a saturated or unsaturated, branched or non-branched hydrocarbon group, preferably with 5 to 20 carbon atoms, which can be substituted with at least one hydroxy group; —X— represents —COO—, —CONH— or —O—, especially carboxylated fatty alcohol ethoxylates and fatty acid amido ethoxylates.

For example, a suitable carboxylated fatty alcohol ethoxylate is designated by the INCI name sodium laureth-13 carboxylate.

For example suitable carboxylated fatty alcohol ethoxylates or fatty acid amido ethoxylates include Akypo Soft® types of Chem-Y, Miranate® LEC or Sandopan® LS-24 (INCI: sodium laureth-13 carboxylate) of Rhone-Poulenc or Clariant.

Additional subject matter of the invention includes a method of using an anionic, carboxylate-group-containing surfactant compound to make a transparent, single-phase composition, which can be put in the form of a foam by a mechanical device. The surfactant compound in this composition is preferably a sulfosuccinate, a sulfosuccinamate, a carboxylated fatty acid amide ethoxylate or a carboxylated fatty alcohol ethoxylate, especially a surfactant compound of the formula I containing a carboxylate group.

Suitable nonionic emulsifiers are, for example, the nonionic emulsifiers listed in "International Cosmetic Ingredient Dictionary and Handbook", 7th Edition, Volume 2, in the section entitled "Surfactants—Emulsifying Agents". The nonionic emulsifiers suitable as the ingredient a2 are preferably ethoxylated fatty acids with 10 to 26 carbon atoms, ethoxylated unihydric or polyhydric alcohols with 1 to 6 carbon atoms, ethoxylated fatty alcohols with 10 to 26 carbon atoms, ethoxylated hydrogenated or non-hydrogenated castor oil, glyceride alkoxylates, fatty acid glyceride polyalkylene glycol ethers or fatty acid partial glyceride polyalkylene glycol ethers, each with less than 30 alkylene glycol units, such as polyethylene glycol (7)-glyceryl cocoate, polyglycol amides, fatty acid sugar esters, ethoxylated fatty acid sugar esters and partial glycerides. The ethoxylation degree of the ethoxylated surfactant compounds usually amounts to from 1 to 400 and is preferably larger than 3.

Suitable ethoxylated fatty acids include, for example, polyethylene glycol (75)-laurate, polyethylene glycol (90)-stearate, polyethylene glycol (120)-stearate, polyethylene glycol (120)-propylene glycol stearate, polyethylene glycol (150)-dilaurate and polyethyene glycol (175)-distearate.

Suitable ethoxylated fatty acid sugar esters include, for example, ethoxylated sorbitan fatty acid ester and polyethylene glycol(120)-methylglucose dioleate.

The partial glycerides include mono- or diglycerides or a mixture of mono- or diglycerides. For example, suitable partial glycerides include polyethylene glycol (30)-glyceryl cocoate, polyethylene glycol (80)-glyceryl cocoate, polyethylene glycol (80)-glyceryl tallowate, polyethylene glycol (120)-glyceryl stearate, polyethylene glycol(200)-glyceryl stearate, poltyethylene glycol(200)-glyceryl tallowate and hydrogenated polyethylene glycol(200)-glyceryl palmitate. Hydrogenated polyethylene glycol (200)-glyceryl palmitate is especially preferred.

In a preferred embodiment only those surfactants and emulsifiers are contained in the composition of the invention that are water-soluble, i.e. those surfactants, which form a clear solution in water at 20° C. when 1% by weight of the surfactant is present in the water. Preferably a composition is preferred which is present in a transparent, clear, single-phase form and in a transparent package. Preferably break-resistant, transparent plastic is used as a packaging material besides glass.

The composition is foamed without help of propellant gases or chemical propellants and is worked into the hair as foam and left in the hair without being rinsed from the hair.

The subject matter of the invention especially includes a mechanical device for foaming the composition according to the invention. The term 'mechanical foaming device' means those devices or apparatus that allows the production of the foam from a liquid without the use of a propellant compound or propellant composition. For example, a commercially available foam pump can be used as the mechanical foaming device or apparatus.

A suitable devices for producing foam are described, for example, in European Patent Application, EP 0 736 462, and the literature cited in it and are obtained, for example, from Yoshino Kogyosho Co., Ltd., Japan. The foam pump Daiwa F2 of Yoshino Kogyosho is especially preferred.

Solvents with a boiling point under 600° C. can be used in the composition (A) accordingto the invention. In a preferred embodiment of the invention the composition of the invention contains at least one polyhydric alcohol, especially one with two to four carbon atoms, such as propylene glycol or glycerol. The solvent is present in an amount of from 0.01 to 50 percent by weight, preferably in an amount of from 2 to 30 percent by weight.

The composition according to the invention can contain additional alcohol, especially a lower alcohol having 1 to 4 carbon atoms, usually used for cosmetic purposes, for example ethanol or isopropanol, in small amounts up to 10 percent by weight. Preferably however the composition according to the invention does not contain this lower alcohol.

Similarly the composition according to the invention can contain solid or waxy polyethylene glycol or polyethylene glycol that is liquid at room temperatures or copolymers of ethylene glycol and propylene glycol.

The composition according to the invention can also contain water-insoluble solvents, for example branched or non-branched hydrocarbon solvents, such as pentane, hexane, isopentane and cyclic hydrocarbons, such as cyclopentane, cyclohexane, paraffins and isododecane. Preferably embodiments of the composition of the invention however contain no such water-insoluble additives.

At least one film-forming, hair-fixing polymer can be used in the hair treatment composition according to the invention in an amount of preferably from 0.01 to 10 percent by weight, especially preferably from 0.1 to 8 percent by weight, as an additional additive ingredient. The polymer can be synthetic or of a natural origin and can be nonionic, anionic or amphoteric. The hair-fixing polymers can be used individually or in a mixture.

The term 'film-forming, hair-fixing polymer' means those polymers which deposit a polymer film on the hair and thus fix the hair when employed in a 0.1 to 5% aqueous, alcoholic or aqueous-alcoholic solution.

If the polymers contain acid groups, they can be partially or completely neutralized with a suitable organic or inorganic base. The preferred bases are primary and secondary amines, especially alkanolamines, such as aminomethylpropanol. If the polymers contain basic groups, they can be partial or completely neutralized with a suitable acid, such as formic acid, pyrrolidone carboxylic acid, lactic acid, etc.

Suitable synthetic, nonionic, film-forming hair-fixing polymers that can be used in the composition according to the invention include homopolymers of vinyl pyrrolidone, homopolymers of N-vinylformamide, copolymers of vinyl pyrrolidone and dimethnylaminoalkylmethacrylates, in which alkyl means methyl, ethyl or propyl, copolymerizates of vinyl pyrrolidone and vinyl acetate, terpolymers of vinyl pyrrolidone and vinyl acetate and vinyl propionate, polyacrylamides, polyvinylalcohols or polyethylene glycol/polypropylene glycol copolymers.

Suitable synthetic film-forming, anionic polymers include, e.g., branched or non-branched vinyl acetate/crotonic acid copolymers, vinyl pyrrolidone/vinyl acrylate copolymers, terpolymers made from acrylic acid, alkyl acrylates and N-alkylacrylamides, especially acrylic acid/ethyl acrylate/N-t-butylacrylamide terpolymers or terpolymers of vinyl acetate, crotonate and vinyl alkanoate, especially vinyl acetate/crotonatelvinyl neodecanoate copolymers and methyl vinyl ether/maleic acid anhydride copolymers and their monoesters.

Natural film-forming polymers or derivatives of them made by chemical transformation can similarly be used in the hair treatment compositions according to the invention. These polymers include polysaccharides or mixtures of oligo-, mono- and disaccharides (C-Pur® 01924 of Cerestar), Chinese pine resin (colophony, rosin), cellulose derivatives, such as hydroxypropyl cellulose with a molecular weight of 30,000 to 50,000 g/mol, or shellac, in neutralized or unneutralized form.

Also amphoteric polymers can be used in the hair treatment composition according to the invention. These amphoteric polymers either have free basic groups, such as amino groups, and free acidic groups, such as carboxyl or sulfonic acid groups, in the molecule and are capable of forming inner salts or they contain both cationic groups, such as the ammonium group, and anionic groups, such as the carboxylate, sulfate or sulfonate groups. The following are especially suitable amphoteric polymers: copolymers formed from alkyacryl amides, especially octylacrylamide, alkylaminoalkylmethacrylate, especially t-butylaminoethylmethacrylate and two or more monomers comprising acrylic acid, methacrylic acid or their esters, such as can be obtained commercially under the trade name Resyn 28-4910 or Amphomer LV-71 of National Starch, USA.

Furthermore water-soluble or water-insoluble silicone compounds can be used in concentrations of from 0.01 to 50 percent by weight, preferably in a concentration of from 0.1 to 5 percent by weight, in the hair treatment composition according to the invention. Volatile and nonvolatile cyclomethicones, dimethicones and dimethicone copolyols are especially preferred. Examples of silicone compounds suitable for use in the composition of the invention include the following: polydimethylsiloxane (dimethicone), α-hydroxy-ω-hydroxypolyoxydimethylsilylene (dimethiconol), cyclic dimethylpolysiloxane (cyclomethicone), trimethyl(octadecyloxy)-silane (stearoxytrimethylsilane), dimethylsiloxane/glycol copolymer(dimethicone copolyol), dimethylsiloxane/aminoalkylsiloxane copolymer with hydroxy terminal groups (amodimethicone), monomethylpolysiloxane with lauryl side chains and polyoxyethylene and/or polyoxypropylene terminal chains, (lauryl methicone copolyol), dimethilsiloxane/glycol copolymer acetate (dimethicone copolyol acetate), dimethylsiloxane/aminoalkyl siloxane copolymer with trimethylsilylene terminal groups (trimethylsilyl amodimethicone). Especially preferred silicone polymers include dimethicone, which is marketed by Wacker, Munich, under the trade name Siloxane F-221 or by Dow Corning Europe, Brussels, under the trade name Dow Corning Fluid 200/0.65 cs; cyclomethicone, which is marketed under the trade name Dow Corning 244 Fluid of Dow Corning Europe or Abil® K4 of Goldschmidt; dimethiconols, which are marketed, for example, under the trade name Silicone Fluid F-212 of Wacker or Unisel® SF-R ofUPI.

The names given in parentheses above correspond to the INCI nomenclature (International Cosmetic Ingredients), as they are defined for cosmetic active ingredients and auxiliary substances.

Also mixtures of silicone polymers are suitable, such as a mixture of dimethicone and dimethiconol, which is sold under the trade name of Dow Corning Fluid 1403 of Dow Corning Europe.

Understandably the compositions according to the invention can also contain conventional cosmetic additive ingredients, such as non-fixing, nonionic polymers, non-fixing anionic polymers and non-fixing, natural polymers as well as their combinations in amounts of preferably from 0.01 to 15 percent by weight; perfume oils in an amount of preferably from 0.01 to 5 percent by weight; turbidity-inducing agents, such as ethylene glycol distearate, styrene/PVP copolymers or polystyrene in an amount of preferably from 0.01 to 5 percent by weight; wetting agents, surface-active ingredients or emulsifiers with or without cleansing action from the classes of anionic, cationic, amphoteric surface-active substances, for example fatty alcohol sulfates, fatty alcohol ether sulfates, fatty acid alkanol amides in an amount of preferably from 0.1 to 20 percent by weight; further moisturizers, dye substances, light protective agents, antioxidants, luster-imparting substances and preservatives in an amount of preferably from 0.01 to 10 percent by weight.

The following examples should more clearly illustrated the invention claimed in the claims appended hereinbelow.

EXAMPLES

Example 1

Hair Treatment Composition for Gentle Shaping

| | |
|---|---|
| 8.00 g | disodium PEG-5 lauryl citrate sulfosuccinate (REWOPOL ® SB CS 50) |
| 15.00 g | hydrogenated castor oil, ethoxylated with 40 mol ethylene oxide (Cremophor ® RH 410) |
| 77.00 g | water |
| 100.00 g | |

The composition forms metastable foam with fine pores by action of foam pump without the help of a propellant. The foam breaks-up without forming a residue when it is worked into the hair and imparts luster and hold to the hair.

Example 2

Hair Treatment Composition for Gentle Shaping

| | |
|---|---|
| 8.00 g | disodium PEG-5 lauryl citrate sulfosuccinate (REWOPOL ® SB CS 50) |
| 5.00 g | glycerol |
| 15.00 g | hydrogenated castor oil, ethoxylated with 40 mol ethylene oxide (Cremophor ® RH 410) |
| 72.00 g | water |
| 100.00 g | |

Example 3

Hair Treatment Composition for Gentle Shaping

| | |
|---|---|
| 8.00 g | disodium ricinol amido MEA sulfosuccinate (REWODERM ® S 1333) |
| 5.00 g | propylene glycol |
| 15.00 g | hydrogenated castor oil, ethoxylated with 40 mol ethylene oxide (Cremophor ® RH 410) |
| 72.00 g | water |
| 100.00 g | |

Example 4

Hair Treatment Composition for Gentle Shaping

| | |
|---|---|
| 8.00 g | disodium PEG-5 lauryl citrate sulfosuccinate (REWOPOL ® SB CS 50) |
| 5.00 g | propylene glycol |
| 15.00 g | hydrogenated castor oil, ethoxylated with 25 mol ethylene oxide (Arlatone ® G) |
| 72.00 g | water |
| 100.00 g | |

Example 5

Hair Treatment Composition for Gentle Shaping

| | |
|---|---|
| 8.00 g | disodium PEG-5 lauryl citrate sulfosuccinate (REWOPOL ® SB CS 50) |
| 5.00 g | propylene glycol |
| 12.00 g | hydrogenated castor oil, ethoxylated with 25 mol ethylene oxide (Arlatone ® G) |
| 1.00 g | hydrogenated glyceryl palmitate, ethoxylated with 200 mol ethylene oxide (REWODERM ® LI S 80) |
| 74.00 g | water |
| 100.00 g | |

Example 6

Hair Treatment Composition for Gentle Shaping

| | |
|---|---|
| 8.00 g | disodium PEG-5 lauryl citrate sulfosuccinate (REWOPOL ® SB CS 50) |
| 5.00 g | propylene glycol |
| 15.00 g | Cremophor ® RH 455 |
| 72.00 g | water |
| 100.00 g | |

Example 7

Hair Treatment Composition for Gentle Shaping

| | |
|---|---|
| 8.00 g | disodium PEG-5 cocamido MIPA-sulfosuccinate (REWOPOL ® SBZ) |
| 5.00 g | propylene glycol |

-continued

| | |
|---|---|
| 15.00 g | hydrogenated castor oil, ethoxylated with 40 mol ethylene oxide (Cremophor ® RH 410) |
| 72.00 g | water |
| 100.00 g | |

Example 8

Hair Treatment Composition for Gentle Shaping

| | |
|---|---|
| 8.00 g | disodium PEG-3 cocamido sulfosuccinate (Beaulight ® A 5000 S) |
| 5.00 g | propylene glycol |
| 15.00 g | hydrogenated castor oil, ethoxylated with 40 mol ethylene oxide (Cremophor ® RH 410) |
| 1.00 g | Cremophor ® EL |
| 71.00 g | water |
| 100.00 g | |

Example 9

Hair Treatment Composition for Gentle Shaping

| | |
|---|---|
| 8.00 g | disodium laureth-3 sulfosuccinate (Texapon ® SB 3) |
| 5.00 g | propylene glycol |
| 15.00 g | hydrogenated castor oil, ethoxylated with 40 mol ethylene oxide (Cremophor ® RH 410) |
| 72.00 g | water |
| 100.00 g | |

Example 10

Hair Treatment Composition for Gentle Shaping

| | |
|---|---|
| 8.00 g | magnesium laureth-11 carboxylate (Akypo Soft ® 100 MgV) |
| 5.00 g | propylene glycol |
| 15.00 g | hydrogenated castor oil, ethoxylated with 40 mol ethylene oxide (Cremophor ® RH 410) |
| 72.00 g | water |
| 100.00 g | |

Example 11

Hair Treatment Composition for Gentle Shaping

| | |
|---|---|
| 8.00 g | sodium laureth-6 carboxylate (Akypo Soft ® 45 NV) |
| 5.00 g | propylene glycol |
| 15.00 g | hydrogenated castor oil, ethoxylated with 40 mol ethylene oxide (Cremophor ® RH 410) |
| 72.00 g | water |
| 100.00 g | |

Example 12

Hair Treatment Composition for Gentle Shaping

| | |
|---|---|
| 8.00 g | sodium laureth-11 carboxylate (Akypo Soft ® 100 BVC) |
| 5.00 g | propylene glycol |
| 15.00 g | hydrogenated castor oil, ethoxylated with 40 mol ethylene oxide (Cremophor ® RH 410) |
| 1.00 g | Tween ® 40 |
| 71.00 g | water |
| 100.00 g | |

Example 13

Hair Treatment Composition for Gentle Shaping

| | |
|---|---|
| 8.00 g | sodium laureth-17 carboxylate (Akypo Soft ® 160 NV) |
| 5.00 g | propylene glycol |
| 15.00 g | hydrogenated castor oil, ethoxylated with 40 mol ethylene oxide (Cremophor ® RH 410) |
| 72.00 g | water |
| 100.00 g | |

Example 14

Hair Treatment Composition for Gentle Shaping

| | |
|---|---|
| 8.00 g | sodium laureth-13 carboxylate (Miranate ® LEC or Sandopan ® LS-24) |
| 5.00 g | propylene glycol |
| 15.00 g | hydrogenated castor oil, ethoxylated with 40 mol ethylene oxide (Cremophor ® RH 410) |
| 1.00 g | Cremophor ® EL |
| 71.00 g | water |
| 100.00 g | |

Example 15

Hair Treatment Composition for Gentle Shaping

| | |
|---|---|
| 8.00 g | disodium PEG-4 cocamido MIPA-sulfosuccinate (REWOPOL ® SBZ) |
| 5.00 g | propylene glycol |
| 15.00 g | hydrogenated castor oil, ethoxylated with 40 mol ethylene oxide (Cremophor ® RH 410) |
| 1.00 g | surfactant 193 (dimethicone copolyol) |
| 72.00 g | water |
| 100.00 g | |

Example 15

COMPARISON OF THE PROPERTIES OF VARIOUS FOAM COMPOSITIONS INCLUDING DIFFERENT SURFACTANT COMPOUNDS

The following hair treatment-relevant properties of the following compositions were determined. The hold of the hair style, its luster, the extent of undesirable after-foaming on working the foam in the hair, foam quality 15 seconds after foam production and foamability of the composition with the help of a foam pump were measured. The measurements were made by testing individual criteria by five persons independently. A value of 1 for a property means 'very good' while a value of 6 means 'unusable'.

Table I shows the composition of the six tested compositions A, B, C, D, E and F. The amount of active surfactant plus emulsifier was maintained constant for all compositions, except for composition F. The ingredients of the compositions were labeled with numbers and a key showing the relationship of the ingredient number to the ingredient is provided here: (1), Arlatone® G; (2), REWO-DERM® S1333; (3), Ampho Betaine AM®; (4), Texapon® N 70; and (5), Oramix® NS 10.

TABLE I

CONTENT OF THE TESTED COMPOSITIONS

| Ingredients | % | % | % | % | % | % |
|---|---|---|---|---|---|---|
| PEG-25 hydrogenated castor oil (1) | 25 | 18 | 18 | 18 | 18 | 18 |
| Disodium ricinolamido MEA sulfosuccinate (2) | 0 | 7 | 0 | 0 | 0 | 0 |
| Cocamidopropyl-Betaine (3) | 0 | 0 | 7 | 0 | 0 | 0 |
| Lauryl ether sulfate 28% (4) | 0 | 0 | 0 | 7 | 0 | 0 |
| Decyl glucoside (5) | 0 | 0 | 0 | 0 | 7 | 0 |
| Glycerol 86% | 5 | 5 | 5 | 5 | 5 | 5 |
| Water | 70 | 70 | 70 | 70 | 70 | 77 |

The results of the testing are shown in the following Table II.

TABLE II

HAIR TREATMENT-RELEVANT PROPERTIES OF THE COMPOSITIONS A TO F

| Property | A | B | C | D | E | F |
|---|---|---|---|---|---|---|
| Foamability | 3 | 1 | 2 | 3 | 3 | 2 |
| Foam quality after 15 seconds | 4 | 2 | 2 | 2 | 3 | 2 |
| After-foaming during application | 1 | 1 | 6 | 6 | 6 | 1 |
| Hold of the Hair style | 1 | 1 | 4 | 3 | 3 | 4 |
| Luster | 2 | 1 | 6 | 6 | 6 | 4 |

A sample of the foam compositions receives an evaluation of 'good' for the property 'foam quality after 15 seconds' when it is as fine-pored as possible 15 seconds after its production and prior to working into the hair and when it breaks up as little as possible. Compositions C, D and E foam very strongly on working into the hair (shampoo effect) so that cleaning of the hair would be required.

The composition according to the invention corresponding to recipe B has essentially better properties for hair treatment than those of the composition A which only contains a nonionic surfactant ingredient and does not have the disadvantages of compositions C, D and E.

When the compositions B, C, D and E are compared with composition F, in which the active content of the Arlatone® G is the same as that of compositions B to E, the fact that the hold of the hair style and luster obtained with composition B according to the invention is significantly better than the other compositions is established.

The disclosure in German Patent Application 198 28 643.0-41 of Jun. 26, 1998 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a single-phase, foam-forming hair treatment composition for producing a pomade effect, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of obtaining a pomade effect on hair, said method comprising the steps of:
   a) providing a product or article of manufacture for hair treatment consisting of a foam pump apparatus and a single-phase composition in the foam pump apparatus, said foam pump apparatus comprising means for making a foam from the single-phase composition; and wherein said single-phase composition comprises at least one anionic, carboxylate-group-containing surfactant compound and at least one nonionic emulsifier;
   b) generating said foam from said single-phase composition without help of a propellant by operating the foam pump apparatus; and
   c) working at least a portion of said foam into the hair and then leaving said at least a portion of said foam in the hair without subsequently rinsing the hair in order to provide the pomade effect.

2. The method as defined in claim 1, wherein said at least one anionic, carboxylate-group-containing surfactant compound is a sulfosuccinate.

3. The method as defined in claim 1, wherein said at least one anionic, carboxylate-group-containing surfactant compound is of the formula (I):

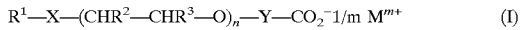

$$R^1—X—(CHR^2—CHR^3—O)_n—Y—CO_2^-1/m\ M^{m+} \quad (I)$$

wherein —X— represents —COO—, —CONH—, —O— or —NH—; —Y— represents an alkylene group or —Y—CO$_2^-$ represents a sulfosuccinate group; $R^1$ represents an unsaturated or saturated, branched or non-branch unsubstituted hydrocarbon group or an unsaturated or saturated, branched or non-branch substituted hydrocarbon group substituted with at least one hydroxy group or $R^1$—X— represents an alkoxylated or non-alkoxylated alkyl citrate group; $R^2$ and $R^3$, independently of each other, represent hydrogen or a methyl group; n is the degree of alkoxylation and is between 0 and 20; M represents one or more counter ions neutralizing negative charge or charges present and m is a counter ion valence.

4. The method as defined in claim 1, wherein said at least one anionic, carboxylate-group-containing surfactant compound is a sulfosuccinate, sulfosuccinamate, carboxylated fatty alcohol ethoxylate, carboxylated fatty acid amide ethoxylate or a mixture thereof.

5. The method as defined in claim 1, wherein said at least one anionic, carboxylate-group-containing surfactant compound is selected from the group consisting of compounds of the formula (II)

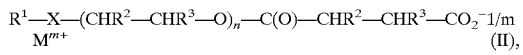

alkyl citrates of the formula (III),

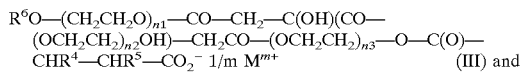

compounds of the general formula (IV)

wherein $R^1$ and $R^6$ each, independently of each other, represent an unsaturated or saturated, branched or non-branch unsubstituted hydrocarbon group with 5 to 20 carbon atoms or an unsaturated or saturated, branched or non-branch substituted hydrocarbon group substituted with at least one hydroxy group and having 5 to 20 carbon atoms; M represents one or more counter ions neutralizing negative charge present and m is a counter ion valence; $R^2$ and $R^3$ each, independently of each other, represents hydrogen or a methyl group, but at least one of said $R^2$ and $R^3$ represents said hydrogen; n represents the degree of alkoxylation and is between 0 and 10; —X— in the formula (II) represents —COO—, —CONH— or —NH— and in the formula (IV) represents —COO—, —CONH— or —O— and the groups $R^4$ and $R^5$, independently of each other, represent hydrogen or $SO_3^-$, but at least one of the groups must be hydrogen; n1, n2 and n3 represent the respective degree of alkoxylation and each is a respective value between 0 and 10.

6. The method as defined in claim 1, wherein said at least one anionic, carboxylate-group-containing surfactant compound is present in an amount of from 0.1 to 30 percent by weight.

7. The method as defined in claim 1, wherein said at least one nonionic emulsifier is selected from the group consisting of ethoxylated fatty acids, ethoxylated unihydric alcohols, ethoxylated polyhydric alcohols, ethoxylated hydrogenated castor oil, ethoxylated non-hydrogenated castor oil, glyceride alkoxylates, fatty acid glyceride polyalkylene glycol ethers, fatty acid partial glyceride polyalkylene glycol ethers, polyglycol amides, fatty acid sugar esters, ethoxylated fatty acid sugar esters and partial glycerides.

8. The method as defined in claim 1, wherein said at least one nonionic emulsifier is present in an amount of from 0.1 to 40 percent by weight.

9. The method as defined in claim 1, wherein said single-phase composition is transparent.

10. The method as defined in claim 1, further comprising a transparent container for said single-phase composition.

11. The method as defined in claim 1, wherein the single-phase composition contains at least one polyhydric alcohol.

12. A method of obtaining a pomade effect on hair, said method comprising the steps of:
   a) providing a product or article of manufacture for hair treatment consisting of a foam pump apparatus and a single-phase composition in the foam pump apparatus, said foam pump apparatus comprising means for making a foam from the single-phase composition; said single-phase composition comprising at least one anionic, carboxylate-group-containing surfactant compound and at least one anionic emulsifier;
   b) generating said foam from said single-phase composition without help of a propellant by operating the foam pump apparatus; and
   c) working at least a portion of said foam into the hair and then leaving said at least a portion of said foam in the hair without subsequently rinsing the hair in order to provide the pomade effect;
   wherein said at least one anionic emulsifier is selected from the group consisting of ethoxylated fatty acids, ethoxylated unihydric alcohols, ethoxylated polyhydric alcohols, ethoxylated hydrogenated castor oil, ethoxylated non-hydrogenated castor oil, glyceride alkoxylates, fatty acid glyceride polyalkylene glycol ethers, fatty acid partial glyceride polyalkylene glycol ethers, polyglycol amides, fatty acid sugar esters, ethoxylated fatty acid sugar esters and partial glycerides;
   wherein said at least one anionic, carboxylate-group-containing surfactant compound is a sulfosuccinate, sulfosuccinamate, carboxylated fatty alcohol ethoxylate, carboxylated fatty acid amide ethoxylate or a mixture thereof.

13. The method as defined in claim 12, wherein said at least one anionic, carboxylate-group-containing surfactant compound is said sulfosuccinate and said at least one nonionic emulsifier is said ethoxylated hydrogenated castor oil or said nonhydrogenated castor oil.

14. A method as defined in claim 12, wherein said at least one nonionic emulsifier is present in an amount of from 0.1 to 40 percent by weight.

15. The method as defined in claim 12, wherein said at least one anionic, carboxylate-group-containing surfactant compound is present in an amount of from 0.1 to 30 percent by weight.

* * * * *